United States Patent [19]
Takle et al.

[11] Patent Number: 6,121,281
[45] Date of Patent: Sep. 19, 2000

[54] AZABICYCLIC CARBAMOYLOXY MUTILIN DERIVATIVES FOR ANTIBACTERIAL USE

[75] Inventors: Andrew Kenneth Takle; Eric Hunt, both of Great Dunmow; Antoinette Naylor, Cheshunt, all of United Kingdom

[73] Assignee: SmithKline Beecham p.l.c., Brentford, United Kingdom

[21] Appl. No.: 09/230,715

[22] PCT Filed: Jul. 29, 1997

[86] PCT No.: PCT/EP97/04166

§ 371 Date: Jan. 29, 1999

§ 102(e) Date: Jan. 29, 1999

[87] PCT Pub. No.: WO98/05659

PCT Pub. Date: Feb. 12, 1998

[30] Foreign Application Priority Data

Aug. 2, 1996 [GB] United Kingdom .................... 9616305
Jun. 19, 1997 [GB] United Kingdom .................... 9712963

[51] Int. Cl.$^7$ .................. A61K 31/439; A61K 31/4375; C07D 453/02; C07D 455/02
[52] U.S. Cl. .................. 514/305; 514/306; 514/325; 514/413; 546/112; 546/133; 546/138; 546/204; 548/452
[58] Field of Search ..................... 546/133, 112, 546/138, 204; 548/452; 514/413, 305, 306, 325

[56] References Cited

FOREIGN PATENT DOCUMENTS

WO97/25309 7/1997 WIPO .

OTHER PUBLICATIONS

Egger et al., "New Pleuromutilin Derivatives With Enhanced Antimicrobial Activity", *The Journal of Antibiotics,* 29(9), p. 923927 (1976).

*Primary Examiner*—Laura L. Stockton
*Attorney, Agent, or Firm*—Edward R. Gimmi; William T. King; Charles M. Kinzig

[57] ABSTRACT

Compounds of formula (3), and pharmaceutically acceptable salts and derivatives thereof, in which $R^1$ is vinyl or ethyl; and $R^2$ is a group $R^3$, $R^4CH_2$—, or $R^5R^6C{=}CH$—; wherein each of $R^3$ and $R^4$ is an azabicyclic ring system or $R^5$ and $R^6$ together with the carbon atom to which they are attached form an azabicyclic ring system, are useful in the prevention and treatment of microbial infections.

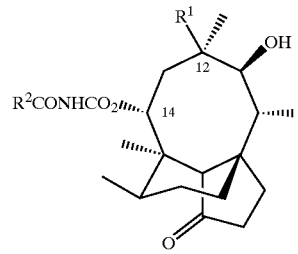

(3)

8 Claims, No Drawings

AZABICYCLIC CARBAMOYLOXY MUTILIN DERIVATIVES FOR ANTIBACTERIAL USE

This application is a 371 of PCT/EP97/04166 filed Jul. 29, 1997.

The present invention relates to novel compounds, to processes for their preparation, to pharmaceutical compositions containing them and to their use in medical therapy, particularly antibacterial therapy.

Pleuromutilin, the compound of formula (1), is a naturally occurring antibiotic which has antimycoplasmal activity and modest antibacterial activity. It has been shown that the antimicrobial activity can be improved by replacing the glycolic ester moiety at position 14 by an R—X—CH$_2$CO$_2$— group, where R is an aliphatic or aromatic moiety and X is O, S, or NR' (H Egger and H Reinshagen, J Antibiotics, 1976, 29, 923). Tiamulin, the compound of formula (2), which is used as a veterinary antibiotic, is a derivative of this type (G Hogenauer in Antibiotics, Vol. V, part 1, ed. F E Hahn, Springer-Verlag, 1979, p.344).

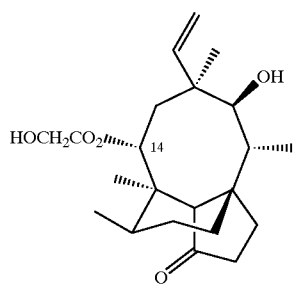

(1)

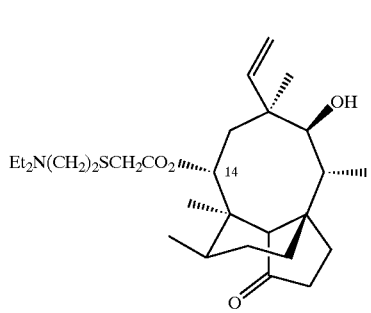

(2)

In this application, the non-conventional numbering system which is generally used in the literature (G Hogenauer, loc.cit.) is used.

We have found that certain novel pleuromutilin analogues containing a 14-O-carbamoyl group, also have improved antimicrobial properties.

Accordingly, in its broadest aspect, the present invention provides a 14-O-carbamoyl derivative of mutilin or 19,20-dihydromutilin, in which the N-atom of the carbamoyl group is acylated by a group which includes an azabicyclic moiety.

More specifically, this invention provides a compound of general formula (3):

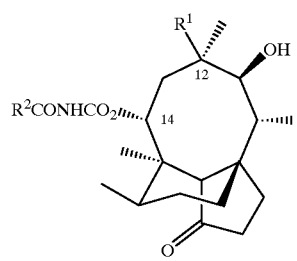

(3)

in which:
R$^1$ is vinyl or ethyl; and
R$^2$ is a group R$^3$, R$^4$CH$_2$—, or R$^5$R$^6$C=CH—; wherein each of R$^3$ and R$^4$ is an azabicyclic ring system or R$^5$ and R$^6$ together with the carbon atom to which they are attached form an azabicyclic ring system.

The azabicyclic ring system is a bridged or fused non-aromatic ring system attached via a bridgehead or non-bridgehead ring carbon atom and containing one bridgehead nitrogen atom as the sole hetero ring atom. The ring system contains between 5 and 10 ring atoms in each ring and is optionally substituted on carbon by up to 3 substituents. Suitable substituents include alkyl, alkyloxy, alkenyl and alkenyloxy, each of which may be carried by either a bridgehead or a non-bridgehead carbon atom. In addition, the bridgehead nitrogen atom may be substituted by oxygen, to form an N-oxide, or by alkyl, to form a quaternary cation. The counterion may be a halide ion such as chloride or bromide, preferably chloride.

The azabicyclic ring system may for example be represented by formula (I):

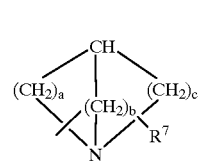

(I)

wherein R$^7$ represents one or more optional substituents as set out above and each of a, b and c is between 0 and 4, such that any one ring has between 5 and 10 ring atoms. The azabicyclic ring system additionally may contain one or more double bonds.

Particular azabicyclic groups include azabicyclo[2.2.2]octyl, azabicyclo[2.2.1]heptyl, azabicyclo[3.2.1 ]octyl, azabicyclo[4.4.0]decyl, quinuclidinyl, azabicyclo[3.2.1]octenyl, and azabicyclo[3.3.1]non-5-yl.

Alkyl and alkenyl groups referred to herein include straight and branched groups containing up to six carbon atoms and are optionally substituted by one or more groups selected from the group consisting of aryl, heterocyclyl, (C$_{1-6}$)alkoxy, (C$_{1-6}$)alkylthio, aryl(C$_{1-6}$)alkoxy, aryl(C$_{1-6}$)alkylthio, amino, mono- or di-(C$_{1-6}$)alkylamino, cycloalkyl, cycloalkenyl, carboxy and esters thereof, hydroxy, and halogen.

Cycloalkyl and cycloalkenyl groups referred to herein include groups having between three and eight ring carbon atoms and are optionally substituted as described hereinabove for alkyl and alkenyl groups.

When used herein, the term "aryl" means single and fused rings suitably containing from 4 to 7, preferably 5 or 6, ring atoms in each ring, which rings. may each be unsubstituted or substituted by, for example, up to three substituents. A fused ring system may include aliphatic rings and need include only one aromatic ring.

Suitable aryl groups include phenyl and naphthyl such as 1-naphthyl or 2-naphthyl.

Suitably any aryl group, including phenyl and naphthyl, may be optionally substituted by up to five, preferably up to three substituents. Suitable substituents include halogen, $(C_{1-6})$alkyl, aryl, aryl$(C_{1-6})$alkyl, $(C_{1-6})$alkoxy, $(C_{1-6})$alkoxy$(C_{1-6})$alkyl, halo$(C1_6)$alkyl, aryl$(C_{1-6})$alkoxy, hydroxy, nitro, cyano, azido, amino, mono- and di-N-$(C_{1-6})$alkylamino, acylamino, arylcarbonylamino, acyloxy, carboxy, carboxy salts, carboxy esters, carbamoyl, mono- and di-N-$(C_{1-6})$alkylcarbamoyl, $(C_{1-6})$alkoxycarbonyl, aryloxycarbonyl, ureido, guanidino, sulphonylamino, aminosulphonyl, $(C_{1-6})$alkylthio, $(C_{1-6})$alkyl sulphinyl, $(C_{1-6})$alkylsulphonyl, heterocyclyl and heterocyclyl $(C_{1-6})$alkyl. In addition, two adjacent ring carbon atoms may be linked by a $(C_{3-5})$alkylene chain, to form a carbocyclic ring.

When used herein the terms "heterocyclyl" and "heterocyclic" suitably include, unless otherwise defined, aromatic and non-aromatic, single and fused, rings suitably containing up to four heteroatoms in each ring, each of which is selected from oxygen, nitrogen and sulphur, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring.

Preferably a substituent for a heterocyclyl group is selected from halogen, $(C_{1-6})$alkyl, aryl$(C_{1-6})$alkyl, $(C_{1-6})$alkoxy, $(C_{1-6})$alkoxy$(C_{1-6})$alkyl, halo$(C_{1-6})$alkyl, hydroxy, amino, mono- and di-N-$(C_{1-6})$alkyl-amino, acylamino, carboxy, carboxy salts, carboxy esters, carbamoyl, mono- and di-N-$(C_{1-6})$alkylcarbonyl, aryloxycarbonyl, $(C_{1-6})$alkoxycarbonyl$(C_{1-6})$alkyl, aryl, oxy groups, ureido, guanidino, sulphonylamino, aminosulphonyl, $(C_{1-6})$alkylthio, $(C_{1-6})$alkylsulphinyl, $(C_{1-6})$alkylsulphonyl, heterocyclyl and heterocyclyl$(C_{1-6})$alkyl.

In a further aspect the present invention provides a method for preparing compounds of the invention, which comprises reacting a compound of formula (4) where X is hydrogen or a hydroxyl protecting group, such as an acyl group, or a compound of formula (5), with an acyl isocyanate of formula $R^3$CONCO, $R^4CH_2$CONCO, or $R^5R^6C$=CHCONCO:

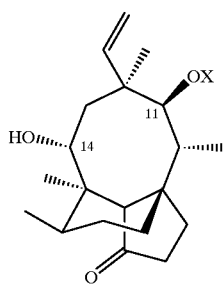

(4)

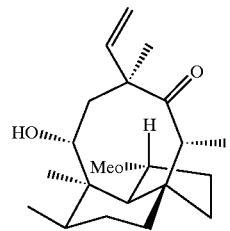

(5)

Methods for preparing acyl isocyantes are described in the literature. For example, they may be prepared by reaction of an acid chloride ($R^3$COCl, $R^4CH_2$COCl, or $R^5R^6C$=CHCOCl) with silver cyanate (e.g. as described by Murdock and Angier in *J. Org. Chem.*, 1962, 27, 3317), tri-n-butyl tin isocyanate (e.g. as described by Akteries and Jochims, *Chem. Ber.*, 1986, 119, 83), or trimethylsilyl isocyanate (e.g. as described by Sheludyakov et al., *J. Gen. Chem. USSR*, 1977, 2061–2067) in an inert solvent such as benzene, toluene, chloroform, dichloromethane, or 1,2-dichloroethane; or reaction of a primary amide ($R^3CONH_2$, $R^4CH_2CONH_2$, or $R^5R^6C$=CHCONH$_2$), or N,N-bis (trimethylsilyl) derivative thereof, with oxalyl chloride or phosgene in an inert solvent (e.g. Speziale and Smith,*J. Org. Chem.*, 1962, 27, 3742; Kozyukov, et al., *Zh Obshch Khim*, 1983, 53, 2155).

We have found that the formation and reaction of the acyl isocyanate can be conveniently carried out in one process. This typically involves reaction of (4) or (5) with an acid chloride (as an acid-addition salt of the azabicyclic moiety, usually the hydrochloride salt) in the presence of silver cyanate and a tertiary base (e.g. triethylamine, diisopropyl ethylamine, pyridine), usually triethylamine, in an inert solvent (e.g. chloroform, dichloromethane, 1,2-dichloroethane).

More particularly, in one aspect the present invention provides a process for the preparation of a compound of formula (3) which comprises reacting a compound of formula (4) with a compound of formula $R^3$COCl, $R^4CH_2$COCl, or $R^5R^6C$=CHCOCl in the presence of silver cyanate and a base, such as triethylamine, wherein each of $R^3$ to $R^6$ is protected where appropriate, and thereafter carrying out one or more of the following steps in any desired order:

deprotecting a group X to generate a hydroxyl group at position 11, deprotecting a protected group $R^3$ to $R^6$, converting one group $R^3$ to $R^6$ to another group $R^3$ to $R^6$, and hydrogenating the vinyl group at position 12 to form an ethyl group.

Although it is possible to prepare compounds of formula (3) by reaction at the 14-hydroxyl in the known compound mutilin (X=H in formula (4)), in practice it is desirable to use an intermediate in which the 11-hydroxyl is protected.

Suitable compounds as formula (4) include 11-O-acyl mutilin derivatives, e.g. mutilin 11-acetate (X=Ac in formula (4)) (A J Birch, C W Holzapfel, R W Richards, Tetrahedron (Suppl.), 1966, 8, Part II, 359) or mutilin 11-dichloroacetate or mutilin 11-trifluoroacetate. After formation of the 14-O-carbamoyl derivative, the 11-O-acyl group may be removed by selective hydrolysis (e.g. using NaOH in MeOH).

In another aspect, the present invention provides a process for the preparation of a compound of formula (3) which comprises reacting a compound of formula (5) with a compound of formula $R^3COCl$, $R^4CH_2COCl$, or $R^5R^6C$=CHCOCl in the presence of silver cyanate and a base, such as triethylamine, wherein each of $R^3$ to $R^6$ is protected where appropriate, and thereafter carrying out one or more of the following steps in any desired order:

treating the product with acid to obtain a compound of formula (3)

deprotecting a protected group $R^3$ to $R^6$, converting one group $R^3$ to $R^6$ to another group $R^3$ to $R^6$, and hydrogenating the vinyl group at position 12 to form an ethyl group.

Formula (5) is (3R)-3-deoxo-11-deoxy-3-methoxy-11-oxo-4-epi-mutilin (H Berner, G Schulz and H Schneider, Tetrahedron, 1980, 36, 1807). After formation of the 14-carbamate, the intermediate may be converted into (3) by treatment with conc. HCl or Lukas reagent (conc. HCl saturated with $ZnCl_2$) in dioxane.

For preparation of 19,20-dihydro analogues (compounds of formula (3) in which $R^1$=Et), before or after the carbamoylation, of a compound of formula (4) or (5), a vinyl group $R^1$ can be reduced by hydrogenation over a palladium catalyst (e.g. 10% Palladium-on-carbon) in a solvent such as ethyl acetate, ethanol, dioxane, or tetrahydrofuran.

Suitable hydroxy, carboxy and amino protecting groups are those well known in the art and which may be removed under conventional conditions and without disrupting the remainder of the molecule. A comprehensive discussion of the ways in which hydroxy, carboxy and amino groups may be protected and methods for cleaving the resulting protected derivatives is given in for example "Protective Groups in Organic Chemistry" (T. W. Greene and P. G. M. Wuts, Wiley-Interscience, New York, 2nd edition, 1991). Particularly suitable hydroxy protecting groups include, for example, triorganosilyl groups such as, for instance, trialkylsilyl and also organocarbonyl and organooxycarbonyl groups such as, for instance, acetyl, allyloxycarbonyl, 4-methoxybenzyloxycarbonyl and 4-nitrobenzyloxycarbonyl. Particularly suitable carboxy protecting groups include alkyl and aryl groups, for instance methyl, ethyl and phenyl. Particularly suitable amino protecting groups include alkoxycarbonyl, 4-methoxybenzyloxycarbonyl and 4-nitrobenzyloxycarbonyl.

In cases where the intermediate of formula (4) (such as X=acetyl) is used, a base-labile protecting group may conveniently be removed at the same time as the group X is deprotected. In cases when the intermediate of formula (5) is used, an acid-labile protecting group may conveniently be removed at the same time as the compound (5) is converted into the compound (3).

The azabicyclic ring system present in the compounds of the present invention may contain a chiral centre, and the compound of formula (3) may therefore comprise a mixture of diastereoisomers or a single diastereoisomer. A single diastereoisomer of formula (3) may be prepared by separating such a mixture of diastereoisomers which has been synthesised using a racemic azabicyclic starting material, or by synthesis using an optically pure azabicyclic starting material.

The compounds of this invention may be in crystalline or non-crystalline form, and, if crystalline, may optionally be hydrated or solvated. When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be present in the crystalline product. This invention includes within its scope stoichiometric hydrates as well as compounds containing variable amounts of water that may be produced by processes such as lyophilisation.

The compounds according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

The present invention also includes pharmaceutically acceptable salts and derivatives of the compounds of the invention. Salt formation may be possible when one of the substituents carries an acidic or basic group. Salts may be prepared by salt exchange in conventional manner Acid-addition salts of the azabicyclic moiety can be pharmaceutically acceptable or non-pharmaceutically acceptable. In the latter case, such salts may be useful for isolation and purification of the compound of formula (3), or intermediates thereto, and will subsequently be converted into a pharmaceutically acceptable salt or the free base. Pharmaceutically acceptable acid-addition salts include those described by Berge, Bighley, and Monkhouse, *J. Pharm. Sci.*, 1977, 66, 1–19. Suitable salts include the hydrochloride, maleate, and methanesulphonate; particularly the hydrochloride.

It will also be understood that where the compound of formula (3) contains a free carboxy moiety, the compound of formula (3) can form a zwitterion.

The compounds of the present invention and their pharmaceutically acceptable salts or derivatives have antimicrobial properties and are useful for the treatment of microbial infections in animals, especially mammals, including humans, in particular humans and domesticated animals (including farm animals). The compounds may be used for the treatment of infections caused by, for example, Gram-positive and Gram-negative bacteria and mycoplasmas, including, for example, *Staphylococcus aureus, Staphylococcus epidermidis, Enterococcus faecalis, Streptococcus pyogenes, Streptococcus agalactiae, Streptococcus pneumoniae,* Haemophilius sp., Neisseria sp., Legionella sp., Chlamydia sp., *Moraxella catarrhalis, Mycoplasma pneumoniae,* and *Mycoplasma gallisepticum.*

The present invention provides a pharmaceutical composition comprising a compound of formula (3) or a pharmaceutically acceptable salt or derivative thereof together with a pharmaceutically acceptable carrier or excipient.

The present invention also provides a method of treating microbial infections in animals, especially in humans and in domesticated mammals, which comprises administering a compound of formula (3) or a pharmaceutically acceptable salt or derivative thereof, or a composition according to the invention, to a patient in need thereof.

The invention further provides the use of a compound of the invention or a pharmaceutically acceptable salt or derivative thereof in the preparation of a medicament composition for use in the treatment of microbial infections.

The compounds and compositions according to the invention may be formulated for administration in any convenient way for use in human or veterinary medicine, by analogy with other antibiotics.

The compounds and compositions according to the invention may be formulated for administration by any route, for example oral, topical or parenteral. The compositions may, for example, be made up in the form of tablets, capsules, powders, granules, lozenges, creams, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, nose drops, nasal sprays, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilised before being filled into a suitable vial or ampoule, which is then sealed. Advantageously, conventional additives including, for example, local anaesthetics, preservatives, and buffering agents can be dissolved in the vehicle. In order to enhance the stability of the solution, the composition may be frozen after being filled into the vial, and the water removed under vacuum; the resulting dry lyophilized powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

A compound or composition according to the invention may suitably be administered to the patient in an antimicrobially effective amount.

A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.0 to 50 mg/kg of body weight. For an adult human (of approximately 70 kg body weight), from 50 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

When the compositions according to the invention are presented in unit dosage form, each unit dose may suitably comprise from 25 to 1000 mg, preferable from 50 to 500 mg, of a compound according to the invention.

The following Examples illustrate the present invention.

Note on naming of pleuromutilin analogues

In the Examples, compound (a), which in the IUPAC system has the systematic name (1S, 2R, 3S, 4S, 6R, 7R, 8R, 14R)-3,6-dihydroxy-2,4,7,14-tetramethyl-4-vinyl-tricyclo [5.4.3.0$^{1,8}$]tetradecan-9-one, is referred to using the trivial name mutilin and with the numbering system described by H Berner, G Schulz, and H Schneider in *Tetrahedron*, 1981, 37, 915–919.

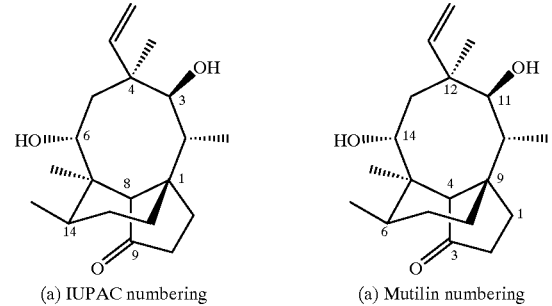

(a) IUPAC numbering      (a) Mutilin numbering

Likewise, compound (b), which has the systematic name (1R, 2R, 4S, 6R, 7R, 8S, 9R, 14R)-6-hydroxy-9-methoxy-2,4,7, 14-tetramethyl-4-vinyl-tricyclo[5.4.3.0$^{1,8}$]tetradecan-3-one, is named as (3R)-3-deoxo-11-deoxy-3-methoxy-11-oxo-4-epi-mutilin; and compound (c), which has the systematic name (1-aza-bicyclo[2.2.2]octane-4-carbonyl)-carbamic acid (1S, 2R, 3S, 4S, 6R, 7R, 8R, 14R)-3-hydroxy-2,4,7,14-tetramethyl-9-oxo-4-vinyl-tricyclo[5.4.3.0$^{1,8}$] tetradec-6-yl ester, is named as (1-aza-bicyclo[2.2.2]octane-4-carbonyl)-carbamic acid mutilin 14-ester.

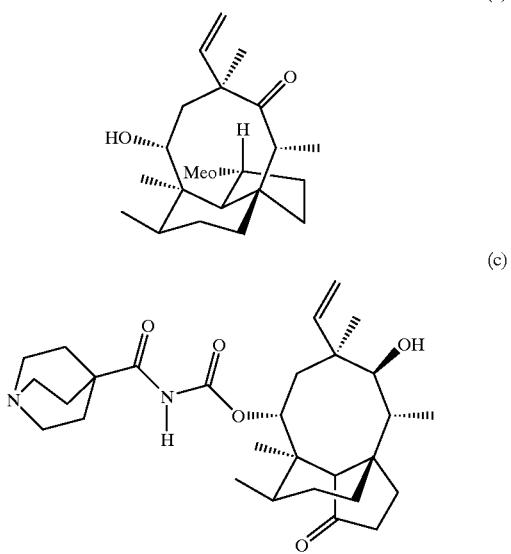

(b)

(c)

EXAMPLE 1

(1-Aza-bicyclo[2.2.2]octane-4-carbonyl)-carbamic acid mutilin 14-ester

Step 1. (1-Aza-bicyclo[2.2.2]octane-4-carbonyl)-carbamic acid (3R)-3-deoxo-11-deoxy-3-methoxy-11-oxo-4-epi-mutilin 14-ester Using the process described in Example 87, Step 3, of PCT/EP96/05874, quinuclidine-4-carboxylic acid hydrochloride (Helvetica Chimica Acta, 1974, 57, 2332) (230 mg) and (3R)-3-deoxo-11-deoxy-3-methoxy-11-oxo-4-epi-mutilin (330 mg) were converted into the title compound, which was obtained as a white foam (160 mg); 1H NMR (CDCl3) inter alia 1.90 (6H, dd, J 8, 7.4 Hz), 3.10 (6H, dd, J 8, 7.4 Hz)), 3.21 (3H, s), 5.00 (1H, d, J 17.5 Hz), 5.27 (1H, d, J 10.7 Hz), 5.77 (1H, d, J 10 Hz), 6.68 (1H, dd, J 17.5, 10.7 Hz), 7.85 (1H, broad s); MS(ES) m/z 515 (MH+).

Step 2. (1-Aza-bicyclo[2.2.2]octane-4-carbonyl)-carbamic acid mutilin 14-ester

Using the process described in Example 87, Step 4, of PCT/EP96/05874, (1-aza-bicyclo[2.2.2]octane-4-carbonyl)-carbamic acid (3R)-3-deoxo-11-deoxy-3-methoxy-11-oxo-4-epi-mutilin 14-ester (140 mg) was converted into the title compound, which was obtained as a white solid (86 mg); 1H NMR (CDCl3) inter alia 0.73 (3H, d, J 6.7 Hz), 0.87 (3H, d, J 7 Hz), 1.17 (3H, s), 1.49 (3H, s), 1.68 (6H, dd, J 8, 7.3 z), 2.93 (6H, dd, J 8, 7.3 Hz), 3.34 (1H, dd, J 10, 6.6 Hz), 5.22 (1H, d, J 17.3 Hz), 5.36 (1H, d, J 11 Hz), 5.76 (1H, d, J 8.5 Hz), 6.54 (1H, dd, J 17.3, 11 Hz); MS(ES) m/z 501 (MH+).

EXAMPLE 2

(1-Aza-bicyclo[2.2.2]octane-4-carbonyl)-carbamic acid mutilin 14-ester hydrochloride (1-Aza-bicyclo[2.2.2]octane-4-carbonyl)-carbamic acid mutilin 14-ester (71 mg) was dissolved in ethyl acetate (5 ml)/1,4-dioxane (2 ml) and 4M HCl in dioxane (0.2 ml) was added. The solution was concentrated to ca. 1 ml by evaporation of solvent under reduced pressure, and toluene (5 ml) was added to give a white precipitate. The precipitate was collected by filtration, washed with toluene (2 ml), and dried in vacuo to give the title compound as a white solid (79 mg); 1 H NMR (D2O) inter alia 0.69 (3H, d, J 6 Hz), 0.92 (3H, d, J 6.8 Hz), 1.15 (3H, s), 1.39 (3H, s), 2.16 (6H, dd, J 8.2,7.5 Hz), 3.42 (6H, dd, J 8.2,7.5 Hz), 3.58 (1H, d, J 6 Hz), 5.20 (1H, d, J 17.5 Hz), 5.28 (1H, d, J 11.1 Hz), 5.68 (1H, d, J 8.1 Hz), 6.36 (1H, dd, J 17.5, 11.1 Hz).

EXAMPLE 3

(1-Aza-bicyclo[2.2.1]heptane-4-carbonyl)-carbamic acid mutilin 14-ester

Step 1. (1-Aza-bicyclo[2.2.1]heptane-4-carbonyl)-carbamic acid (3R)-3-deoxo-11-deoxy-3-methoxy-11-oxo-4-epi-mutilin 14-ester Using the process described in Example 87, Step 3, of PCT/EP96/05874, 1-azabicyclo[2.2. 1]heptane-4-carboxylic acid hydrochloride (Chemical Abstracts, 1989, 110, 95016) (700 mg) and (3R)-3-deoxo-11-deoxy-3-methoxy-11-oxo-4-epi-mutilin (1 g) were converted into the title compound, which was obtained as a white solid (330 mg); 1H NMR (CDCl3) inter alia 2.05 (4H, m), 2.72 (4H, m), 3.08 (2H, m), 3.22 (3H, s), 3.44 (1H, m), 5.02 (1H, d, J 17.5 Hz), 5.30 (1H, d, J 11.6 Hz), 5.80 (1H, d, J 9.9 Hz), 6.69 (1H, dd, J 17.5, 11.6 Hz). 7.48 (1H, s); MS(ES) m/z 501 (MH+).

Step 2. (1-Aza-bicyclo[2.2.1]heptane-4-carbonyl)-carbamic acid mutilin 14-ester

Using the process described in Example 87, Step 4, of PCT/EP96/05874, (1-Aza-bicyclo[2.2.1]heptane-4-carbonyl)-carbamic acid (3R)-3-deoxo-11-deoxy-3-methoxy-11-oxo-4-epi-mutilin 14-ester (300 mg) was converted into the title compound, which was obtained as a white solid (250 mg); 1H NMR (CDCl3) inter alia 2.28 (4H, m), 3.06 (2H, m), 3.37 (1H, broad s), 5.24 (1H, dd, J 17,3, 1.4 Hz), 5.38 (1H, dd, J 11, 1.4 Hz), 5.78 (1H, d, J 8.5 Hz), 6.64 (1H, dd, J 17.3, 11 Hz), 7.38 (1H, s); MS(EI) m/z 486 (M+); Found: 486.3085, C28H42N2O5 requires 486.3094.

EXAMPLE 4

{(3S,4R)-1-Aza-bicyclo[2.2.1]heptane-3-carbonyl}-carbamic acid mutilin 14-ester

Step 1. {(3S,4R)-1-Aza-bicyclo[2.2.1]heptane-3-carbonyl}-carbamic acid (3R)-3-deoxo-11-deoxy-3-methoxy-11-oxo-4-epi-mutilin 14-ester (3R)-3-Deoxo-11-deoxy-3-methoxy-11-oxo-4-epi-mutilin (490 mg, 1.46 mmol) was combined with (3S,4R)-1-azabicyclo[2.2.1]heptane-3-carbonyl chloride (280 mg, 1.46 mmol) and silver cyanate (550 mg, 3.67 mmol) in dry dichloromethane (20 ml). Triethylamine (0.20 ml, 1.46 mmol) was added and the reaction stirred at room temperature for 16 hours in subdued light and under an atmosphere of argon. The mixture was filtered through Kieselguhr and the filtrate washed with saturated aqueous sodium hydrogen carbonate (×2) and brine. After drying (MgSO$_4$) purification was accomplished by chromatography on silica gel eluting with 4% (9:1 methanol:ammonia (35%)) in dichloromethane to yield the title compound (276 mg, 38%); nmax (CH2Cl2) 3383, 2981, 1780, 1749, 1698, 1460 and 1374 cm−1; MS (EI) m/z 500 (M+). Found: 500.3248, C29H44N2O5 requires 500.3250.

Step 2. {(3S,4R)-1-Aza-bicyclo[2.2.1]heptane-3-carbonyl}-carbamic acid mutilin 14-ester The product of Step 1 (260 mg, 0.52 mmol) in dioxane (3 ml) was treated with conc. HCl (3 ml) and the reaction stirred at room for 30 minutes. The solution was diluted with water and washed with dichloromethane (×2). The aqueous phase was basified with saturated aqueous sodium hydrogen carbonate and the product extracted into dichloromethane. The organic phase was dried (MgSO4) and concentrated to yield the title compound (187 mg, 74%); nmax (CH2Cl2) 3386,2962, 1782, 1735, 1699 and 1467cm−1; 1H NMR (d6-DMSO) 0.63 (3H, d, J 6.6 Hz), 0.81 (3H, d, J 7.0 Hz), 1.05–3.12 (29H, m) including 1.09 (3H, s) and 1.42 (3H, s), 4.52 (1H, d, J 6.0 Hz, exch), 5.03–5.12 (2H, m), 5.51 (1H, d. J 7.8 Hz), 6.21 (1H, dd, J 17.7, 11.1 Hz), 10 40 (1 H, bs); MS(Cl) m/z 487 (MH+).

EXAMPLE 5
{(3S,4R)-1-Aza-bicyclo[2.2.1]heptane-4-carbonyl}-carbamic acid 14-deoxy-19,20-dihydro-mutilin 14-ester A solution of {(3S,4R)-1-aza-bicyclo[2.2.1]heptane-4-carbonyl}-carbamic acid mutilin 14-ester (95 mg, 0.20 mmol) in 1:1 ethanol:tetrahydrofuran (10 ml) was hydrogenated for 12 hours over 10% palladium on carbon (90mg). The solution was filtered through celite and the solvent evaporated in vacuo to yield the title compound (85 mg, 87%); nmax (KBr) 3421, 2957, 1772, 1733, 1702 and 1464cm−1; 1H NMR (d6-DMSO) inter alia 0.68 (3H, d. J 7.1 Hz), 0.82 (3H, d, J 6.8 Hz), 4.46 (1H, d, J 5.9 Hz), 5.46 (1H, d, J 7.6 Hz), 10 53 (1H, bs); MS (EI) m/z 488 (M+). Found: M+, 488.3256; C28H44N2O5 requires 488.3250.

EXAMPLE 6
(1-Aza-bicyclo[2.2.2]octane-4-carbonyl)-carbamic acid 14-deoxy-19,20-dihydro-mutilin 14-ester A solution of (1-aza-bicyclo[2.2.2]octane-4-carbonyl)-carbamic acid mutilin 14-ester (100 mg, 0.20 mmol) in 2:1 tetrahydrofuran:ethanol (30 ml) was hydrogenated for 1 hour over 10% palladium on carbon (10 mg). The solution was filtered through celite and the solvent evaporated in vacuo to yield the title compound as a white solid (90 mg, 90%); nmax(CH2Cl2) 2960, 1782, 1733, 1716 and 1479cm−1; 1H NMR (CDCl3) inter alia 0.69 (3H, d, J 6.6 Hz), 3.42 (1H, d, J 5.9 Hz), 5.61 (1H, d, J 8.2 Hz), 7.37 (1H, bs); MS (EI) m/z 502 (M+). Found: M+, 502.3411; C29H46N2O5 requires 502.3407.

EXAMPLE 7
(1-Aza-bicyclo[2.2.2]octane-3-carbonyl)-carbamic acid mutilin 14-ester Step 1. (1-Aza-bicyclo[2.2.2]octane-3-carbonyl)-carbamic acid (3R)-3-deoxo-11-deoxy-3-methoxy-11-oxo-4-epi-mutilin 14-ester Quinuclidine-3-carboxylic acid was converted to the acid chloride hydrochloride by the procedure described in Example 161 of PCT/EP96/05874. This acid chloride was then reacted with (3R)-3-deoxo-11-deoxy-3-methoxy-11-oxo-4-epi-mutilin (1.002 g) by the procedure outlined in Example 161 of PCT/EP96/05874, to yield the title compound as a colourless foam (1.116 g) after silica gel column chromatography; MS (ES) m/z 515 (MH+).

Step 2. (1-Aza-bicyclo[2.2.2]octane-3-carbonyl)-carbamic acid mutilin 14-ester

The product from Step 1, (1.13 g) in 1,4-dioxan (12 ml) was stirred at room temperature for 7 h with conc. hydrochloric acid (5 ml). The solution was then diluted with ethyl acetate and neutralized with saturated sodium hydrogen carbonate solution. The organic solution was washed with saturated sodium chloride solution, dried (MgSO4) and evaporated to yield the crude product. After purification by silica gel chromatography, eluting with a gradient of 0–20% 9:1 methanol/35% ammonia solution in dichloromethane, the title compound was isolated as a white solid, (0.340 g). This solid, which was a mixture of two diastereoisomers, was digested in hot ethyl acteate and the resulting white solid was collected by filtration to yield one pure diastereoisomer of the title compound (0.140 g); 1H NMR inter alia (CDCl3) 0.75 (3H, d, J 6.5 Hz), 0.90 (3H, d, J 7.0 Hz), 1.20 (3H, s), 1.40 (3H, s), 2.70–3.10 (5H, m), 3.20–3.42 (3H, m), 5.15–5.40 (2H, ddd), 5.70 (1H, d, J 8.3 Hz), 6.50 (1H, dd, J 10.95, 17.4 Hz) and 7.40 (1H, s); MS (ES) m/z 501 (MH+). The mother liquors contained predominantly the other diastereoisomer of the title compound (0.200 g); 1 H NMR inter alia (CDCl3) 0.75 (3H, d, J 6.5 Hz), 0.90 (3H, d, J 7.0 Hz), 1.20 (3H, s), 1.41 (3H, s), 2.12–2.4 (3H, m), 2.70–3.10 (5H, m), 3.24–3.42 (3H, m), 5.15–5.45 (2H, m), 5.69 (1H, d, J 8.3 Hz), 6.50 (1H, dd, J 11.0, 17.35 Hz) and 7.40 (1H, s); MS (ES) m/z 501 (MH+).

EXAMPLE 8
{(3S,4R)-1-Aza-bicyclo[2.2.1 ]heptane-3-carbonyl}-carbamic acid mutilin 14-ester hydrochloride A solution of {(3 S,4R)-1-aza-bicyclo[2.2.1]heptane-3-carbonyl}-carbamic acid mutilin 14-ester (1.0 g; 2.06 mmol) in acetone (100 ml) was treated with 1M HCl in diethyl ether (4.2 ml; 4.20 mmol). The solution was stirred for 1 hour at room temperature and then concentrated in vacuo. The residue was triturated with diethyl ether to yield the title compound as a white solid (1.02 g, 95%); nmax (KBr) 3421, 2924, 1772, 1734, 1704 and 1465cm−1; 1H NMR (D20) inter alia 0.62 (3H, d, J 6.0 Hz), 0.90 (3H, d, J 6.9 Hz), 5.22 (2H, dd, J 16.7, 11.1 Hz), 5.61 (1H, d, J 8.1 Hz), 6.35 (1H, dd, J 17.5, 11.1 Hz).

EXAMPLE 9
(1-Aza-bicyclo[3.2.1]octane-5-carbonyl)-carbamic acid mutilin 14-ester Step 1. (1-Aza-bicyclo[3.2.1]octane-5-carbonyl)-carbamic acid (3R)-3-deoxo-11-deoxy-3-methoxy-11-oxo-4-epi-mutilin 14-ester Triethylamine (0.58 ml, 4.2 mmol) was added to a stirred mixture of racemic 1-azabicyclo[3.2.1]octane-5-carbonyl chloride hydrochloride (4 mmol), (3R)-3-deoxo-11-deoxy-3-methoxy-11-oxo-4-epi-mutilin (668 mg, 2 mmol) and silver cyanate (600 mg) in dichloromethane (25 ml). The mixture was stirred overnight at room temperature, filtered and the filtrate evaporated to dryness. The crude product was purified by chromatography on silica gel, eluting with 35% ammonia solution:methanol:dichloromethane 1:9:90 to give the title compound as a white solid (480 mg), Rf 0.1; 1H NMR (CDCl3) inter alia 7.4 (1H, br s), 5.79 (1H, d, J 10), 3.21 (3H, s), 2.75–3.0 (6H, m); MS (+ve ion electrospray) m/z 515 (30%, MNH4+), m/z 556 (100%, M+H+MeCN+).

Step 2.(1-Aza-bicyclo[3.2.1]octane-5-carbonyl)-carbamic acid mutilin 14-ester

The product of Step 1 (480 mg, 0.93 mmol) was dissolved in dioxan (2.5 ml) and conc hydrochloric acid (2.5 ml) was added slowly with cooling in an ice bath. The clear solution was stirred at room temperature for 4 hours and then diluted with water and basified by addition of sodium carbonate. The mixture was extracted with ethyl acetate and washed with brine. Drying (MgSO4) and evaporation gave a crude product which was purified by chromatography on silica gel eluting with 35% ammonia solution:methanol:dichloromethane 1:9:90, giving two diastereoisomers of the title compound as a white solid (274 mg, 58%); Rf 0.08; n max (CHCl3) 2962, 1772, 1736m, 1628cm−1; 1H NMR(CDCl3) inter alia 7.58 (1H, br s), 6.51 (1H, dd, J 17, 11), 5.75 (1H, d, J 8.4), 5.34 (1H, dd, J 11, 1.25), 5.19 (1H, d, J 17, 1.25), 3.36 (1H, br), 3.08–3.2 (1H, m), 2.7–3.05 (5H, m); MS (+ve ion electrospray) m/z 501 (100%, MH+), MS (−ve ion electrospray) m/z 499 (100%, M−H−).

EXAMPLE 10
(1-Aza-bicyclo[2.2.2]octane-2-carbonyl)-carbamic acid mutilin 14-ester Step 1. (1-Aza-bicyclo[2.2.2]octane-2-carbonyl)-carbamic acid (3R)-3-deoxo-11-deoxy-3-methoxy-11-oxo-4-epi-mutilin 14-ester Triethylamine (0.2 ml, 1.5 mmol) was added to a stirred mixture of racemic 1-azabicyclo[2.2.2]octane-2-carbonyl chloride hydrochloride (ca 3 mmol), (3R)-3-deoxo-11- deoxy-3-methoxy-11-oxo-4-epi-mutilin (501 mg, 1.5 mmol) and silver cyanate (225 mg) in dichloromethane (10 ml). The mixture was stirred overnight at room temperature, filtered and the filtrate diluted with dichloromethane and washed with aq sodium bicarbonate and with brine. Drying (MgSO4) and evaporation gave a crude product which was purified by chromatography on silica gel, eluting with ethyl acetate: n-hexane 1:1. The title compound was obtained as a colourless gum (220 mg), Rf 0.12.

Step 2. (1-Aza-bicyclo[2.2.2]octane-2-carbonyl)-carbamic acid mutilin 14-ester

The product of Step 1 (200 mg) was dissolved in dioxan (2 ml) and conc hydrochloric acid (2 ml) was added slowly with cooling in an ice bath. The clear solution was stirred at room temperature for 3 hours and then diluted with water and basified by addition of sodium bicarbonate. The mixture was extracted with ethyl acetate and washed with brine. Drying (MgSO4) and evaporation gave a crude product which was purified by chromatography on silica gel eluting with 5% methanol in chloroform, giving two diastereoisomers of the title compound as a white foam (135 mg, 69%); Rf 0.08; n max (CHCl3) 3309, 2946, 1780, 1735m, 1713 cm−1; MS (+ve ion electrospray) m/z 501 (22%, MH+), MS (−ve ion electrospray) m/z 499 (100%, M−H−).

EXAMPLE 11

{(3R,4S)-1-Aza-bicyclo[2.2.1]heptane-3-carbonyl}-carbamic acid mutilin 14-ester

Step 1. {(3R,4S)-1-Aza-bicyclo[2.2.1]heptane-3-carbonyl}-carbamic acid (3R)-3-deoxo-11-deoxy-3-methoxy-11-oxo-4-epi-mutilin 14-ester Ethyl (3R,4S)-1-azabicyclo[2.2.1]heptane-3-carboxylate (2.0 g, I. F. Cottrell, D. Hands, D. J. Kennedy, K. J. Paul, S. H. B. Wright and K. Hoogsteen, *J. Chem. Soc. Perkin Trans.* 1, 1991, 1091–1097) was dissolved in concentrated hydrochloric acid and heated under reflux for 5 hours. After cooling the solution was evaporated under reduced pressure and the residue re-evaporated from toluene (×3). Drying over phosphorous pentoxide and trituration with cold ethyl acetate/methanol gave the hydrochloride salt of (3R,4S)-1-azabicyclo[2.2.1]heptane-3-carboxylic acid (1.2g).

Using the process of Example 161 Step 1 of PTC/EP96/05874 (3R,4S)-1-azabicyclo[2.2.1]heptane-3-carboxylic acid hydrochloride (890 mg) and (3R)-3-deoxo-11-deoxy-3-methoxy-11-oxo-4-epi-mutilin (1.67 g) were converted to the title compound, which was obtained as a colourless solid (1.28g, 51%): 1H NMR (CDCl3) inter alia 0.86 (3H, d, J 7.0 Hz), 1.01 (3H, d, J 6.3 Hz), 1.21 (3H, s), 1.24 (3H, s), 3.23 (3H, s), 5.05 (1H, d, J 17.5 Hz), 5.34 (1H, d, J 10.7 Hz), 5.76 (1H, d, J 10.0 Hz), 6.62 (1H, dd, J 17.5, 10.7 Hz), 7.75–7.85 (1H, br exch); MS(Electrospray) m/z 501 (MH+).

Step 2. {(3R,4S)-1-Aza-bicyclo[2.2.1]heptane-3-carbonyl}-carbamic acid mutilin 14-ester The product of Step 1 (501 mg) in dioxane (5 ml) was treated with concentrated hydrochloric acid (5 ml) and the reaction stirred at room for 3 hours. The solution was diluted with water and washed with ethyl acetate. The aqueous phase was basified with saturated aqueous sodium hydrogen carbonate and the product extracted into chloroform. The organic phase was washed with water and saturated sodium chloride solution, dried (MgSO4) and concentrated. Purification of the residue by chromatography on silica gel eluting with chloforn/methanol/35% aqueous ammonia solution (20:1:0.1) gave the title compound as a colourless solid (380 mg, 78%): [α]D$^{20}$-8.0° (c. 0.5; EtOH); nmax (CH2Cl2) 3386, 2962, 1782, 1735, 1699 and 1467cm−1; 1H NMR (CDCl3) inter alia 0.76 (3H, d, J 6.5 Hz), 0.90 (3H, d, J 6.8 Hz), 1.20 (3H, s). 1.45 (3H, s), 5.24 (1H, dd, J 17.3 Hz), 5.38 (1H, d, J 11.0 Hz), 5.73 (1H, d, J 8.5 Hz). 6.49 (1H, dd, J 17.3, 11.0 Hz), 7.70–7.90 (1H, br exch); MS(Electrospray) m/z 487 (MH+).

EXAMPLE 12

{(3R,4S)-1-Aza-bicyclo[2.2.1 ]heptane-3-carbonyl}-carbamic acid mutilin 14-ester hydrochloride A solution of {(3R,4S)-1-aza-bicyclo[2.2.1]heptane-3-carbonyl}-carbamic acid mutilin 14-ester (200 mg) in acetone (15 ml) was treated with 1M hydrogen chloride in diethyl ether (0.8 ml). The solution was stirred for 1 hour at room temperature. The resulting solid was collected washed with diethyl ether and dried to give the title compound as a colourless solid (200 mg, 93%): [α]D$^{20}$-17.4° (c. 0.5; EtOH); δ(D$_2$O) inter alia 0.62 (3H, d, J 5.8 Hz), 0.85 (3H, d, J 7.0 Hz), 1.08 (3H, s), 1.32 (3H, s), 5.13 (1H, d, J 17.5 Hz), 5.20 (1H, d, J 11.0 Hz), 5.56 (1H, d, J 8.0 Hz), 6.30 (1H, dd, J 17.5 and 11.0 Hz); MS (Electrospray) m/z 487 (MH+-HCl, 100%).

EXAMPLE 13

{(3R,4R)-1-Aza-bicyclo[2.2.1]heptane-3-carbonyl}-carbamic acid mutilin 14-ester hydrochloride A suspension of (3R,4R)-1-azabicyclo[2.2.1]heptane-3-carboxylic acid hydrochloride (1.91g, crude, containing NaCl, prepared according to G. A. Showell, R. Baker, J. Davies, R. Hargreaves, S. B. Freedman, K. Hoogsteen, S. Patel and R. J. Snow, *J. Med. Chem.* (1992), 35, 911–916) in dichloromethane (25 ml) was stirred under argon and treated with DMF (2 drops) and oxalyl chloride (1.56 ml). After 3 hours the solvent was evaporated, benzene (20 ml) added and evaporated, and dry dichloromethane (25 ml) added. The suspension was stirred under argon and treated with (3R)-3-deoxo-11-deoxy-3-methoxy-11-oxo-4-epi-mutilin (1.64g, prepared according to H. Berner, G. Schulz and H. Schneider, *Tetrahedron* (1980), 36, 1807), silver cyanate (925 mg) and triethylamine (0.86 ml). After 14 hrs saturated aqueous NaHCO$_3$ (25 ml) was added and stirred vigorously. The mixture was filtered through celite, the layers separated and the organic layer dried and evaporated. The residue was chromatographed on silica, eluting with dichloromethane/methanol/35% aqueous NH$_4$OH (19:1:0.1) to yield {(3 R,4R)-1-aza-bicyclo[2.2.1]heptane-3-carbonyl}-carbamic acid (3R)-3-deoxo-11-deoxy-3-methoxy-11-oxo-4-epi-mutilin 14-ester (0.88g): υ$_{max}$ (CHCl$_3$)3393, 1781, 1752, 1697, 1466 cm$^{-1}$; MS(+ve ion electrospray)m/z 501. (MH$^+$, 100%).

This material was suspended in dioxan (12 ml), stirred, ice-cooled and treated with conc. HCl (8 ml). After 5 mins, the cooling bath was removed and the solution left for 4 hours. Ethyl acetate (30 ml) and water (30 ml) were added, followed by solid NaHCO$_3$ portionwise until basic. The layers were separated and the organic layer dried and evaporated. The residue was taken up in ethyl acetate (20 ml) and treated with a 1M solution of HCl in ether (3.5 ml), the solvent evaporated and the residue triturated under ether. Filtration gave the title compound as a white solid (660 mg): [α]D$^{20}$+2.8° (c. 0.5; EtOH); υ$_{max}$ (CHCl$_3$) 3548, 3432, 2429 (broad), 2361 (broad), 1724, 1581 cm$^{-1}$; δ(DMSO) inter alia 0.65 (3H, d, J 6.3 Hz), 0.82 (3H, d, J 6.8 Hz), 2.41 (1H, s), 4.58 (1H. broad s, disappears on D$_2$O exchange), 5.0–5.2 (2H, m), 5.49 (1H, d, J 7.5 Hz), 6.23 (1H, dd, J 11 and 17.5 Hz), 10.68 (1H, s, disappears on D$_2$O exchange), 10.78 (1H, s, disappears on D$_2$O exchange); MS (+ve ion electrospray) m/z 487 (MH$^+$-HCl, 100%).

The following compounds were prepared in a similar manner to Example 13:

EXAMPLE 14

{(3S,4S)-1-Aza-bicyclo[2.2.1]heptane-3-carbonyl}-carbamic acid mutilin 14-ester hydrochloride (3S,4S)-1- azabicyclo[2.2.1]heptane-3-carboxylic acid hydrochloride was prepared according to G. A. Showell, R. Baker, J. Davies, R. Hargreaves, S. B. Freedman, K. Hoogsteen, S. Patel and R. J. Snow, *J. Med. Chem.* (1992), 35, 911–916. The free base {(3S,4S)-1-aza-bicyclo[2.2.1]heptane-3-carbonyl}-carbamic acid mutilin 14-ester was chromatographed on silica, eluting with dichloromethane/methanol/35% aqueous NH$_4$OH (19:1:0.1) before conversion to the hydrochloride. The title compound was obtained as a white solid: [α]D$^{20}$+11° (c. 0.5; EtOH); υ$_{max}$ (CDCl$_3$) 3695, 3387,2426 (broad), 2360 (broad) 1736, 1711, 1602 cm$^{-1}$; δ(DMSO) inter alia 0.64 (3H. d, J 6.3 Hz), 0.81 (3H, d. J 6.8 Hz), 2.40 (1H. s), 4.57 (1H, d, J 5.8 Hz), disappears on D$_2$O exchange), 5.0–5.2 (2H, m), 5.49 (1H, d, J 7.8 Hz), 6.20 (1H, dd, J 8.6 and 17.5 Hz), 10.68 (1H, s, disappears on D$_2$O exchange), 10.78 (1H, s, disappears on D$_2$O exchange) MS (ammonia chemical ionisation) m/z 487 (MH$^+$-HCl, 100%).

EXAMPLE 15
(1-Aza-bicyclo[4.4.0]decane-4-carbonyl)-carbamic acid mutilin 14-ester hydrochloride (equatorial isomers)

The title compound was prepared from the equatorial isomer of 1-azabicyclo [4.4.0]decane-4-carboxylic acid hydrochloride (P. A. Wyman et al, *Bioorg. and Med. Chem.* (1996), 4 255–261) and isolated as a white solid (35% overall): δ(DMSO) inter alia 0.63 (3H, d, J 6.3 Hz), 0.82 (3H, d, J 6.3 Hz), 4.55 (1H, d, J 5.8 Hz, disappears on D$_2$O exchange) 5.03–5.13 (2H, m), 5.50 (1H, d, J 7.8 Hz), 6.21 (1H, dd, J 11.3 and 17.7 Hz), 10.1 (1H, broad s, disappears on D$_2$O exchange), 10.52 (1H, s, disappears on D$_2$O exchange); MS (+ve ion electrospray) 529 (MH$^+$, 100%).

EXAMPLE 16
(1-Aza-bicyclo[4.4.0]decane-4-carbonyl)-carbamic acid mutilin 14-ester hydrochloride (axial isomers)

The title compound was prepared from the axial isomer of 1-azabicyclo[4.4.0]decane-4-carboxylic acid hydrochloride (P. A. Wyman et al, *Bioorg. Med. Chem.*, (1996), 4, 255–261) and isolated as a white solid (6% overall yield): δ(DMSO) inter alia 0.63 (3H, d, J 6.3 Hz), 0.82 (3H, d, J 6.4 Hz), 3.43 (1H, t collapses to d on D$_2$O exchange, J 5.3 Hz), 4.54 (1H, d, J 6 Hz, disappears on D$_2$O exchange), 5.03–5.15 (2H, m), 5.50 (1H, d, J 8 Hz), 6.21 (1H, dd, J 11.3 Hz, 17.7 Hz), 10.12 (1H, broad s, disappears on D$_2$O exchange), 10.52 (1H, s, disappears on D$_2$O exchange); MS (+ve ion electrospray) m/z 529 (MH$^+$, 100%)

EXAMPLE 17
{(1-Aza-bicyclo[4.4.0]dec-4-yl)-acetyl}-carbamic acid mutilin 14-ester Equatorial ethyl 1-azabicyclo[4.4.0]dec-4-yl-acetate (U.S. Pat. No. 3,692,791) was hydrolysed with 8M hydrochloric acid (1 day at room temp.). The resulting equatorial (1-azabicyclo[4.4.0]dec-4-yl)-acetic acid hydrochloride was used to prepare the title compound as a solid (21% overall): δ(CDCl$_3$) inter alia 5.17 (1H, d, J 17.5 Hz), 5.31 (1H, d, J 12.5 Hz), 5.63 (1H, d, J 7.5 Hz). 6.41 (1H, dd, J 17.5 and 12.5 Hz), 7.27 (1H, s); MS (+ve ion electrospray) m/z 543 (MH$^+$, 100%).

EXAMPLE 18
(1-Aza-bicyclo[3.2.1]oct-3-ene-3-carbonyl)-carbamic acid mutilin 14-ester The title compound was prepared from 1-azabicyclo[3.2.1]oct-3-ene-3-carboxylic acid hydrochloride (S. M. Bromidge et al, *Bioorg. and Med. Chem. Letters*, (1994), 4, 1185–1190) to give a white solid (12% overall): δ(CDCl$_3$) inter alia 0.76 (3H, d, J 7.5 Hz), 0.88 (3H, d, J 5 Hz), 3.95 (1H, d, J 17.5 Hz), 5.21 (1H, dd, J 17.5 Hz, 2 Hz), 5.36 (1H, dd, J 10 Hz, 2 Hz), 5.78 (1H, d, J 7.5 Hz), 6.52 (1H, dd, J 17.5 Hz, 10 Hz), 6.91 (1H, d, 7.5 Hz), 7.41 (1H, s); MS (+ve ion electrospray) m/z 499 (MH$^+$, 100%).

EXAMPLE 19
(1-Aza-bicyclo[3.3.1]nonane-5-carbonyl)-carbamic acid mutilin 14-ester The title compound was prepared from 1-azabicyclo [3.3.1]nonane-5-carboxylic acid (U.S. Pat. No. 573,216, July 1992) as a solid (19% overall): δ(CDCl$_3$) inter alia 3.27 (1H, d), 5.12 (1H, dd), 5.27 (1H, dd), 5.68 (1H, d), 6.46 (1H, dd); MS (+ve ion electrospray) m/z 515 (MH$^+$)

EXAMPLE 20
{(1-Aza-bicyclo[2.2.2]oct-3-ylidene)-acetyl}-carbamic acid mutilin 14-ester 3-Ethoxycarbonylmethylene-1-azabicyclo[2.2.2]octane (E,Z mixture; L. N. Yakhontov, L. I. Mastafanova, M. V. Rubstov, Zh. Obshch. Khim. (1963), 33, 3211–3214) was hydrolysed with 8M hydrochloric acid (2 days room temp. followed by 1 hour reflux). The resulting (1-aza-bicyclo [2.2.2]oct-3-ylidene)-acetic acid (E, Z mixture) was used to prepare the title compound as a solid (17% overall, consisted of a single double bond isomer): δ(CDCl$_3$) inter alia 5.24 (1H, d, J 17.4 Hz), 5.39 (1H, d, J 11.0 Hz), 5.71 (1H, d, J 8.4 Hz), 6.52 (1H, dd, J 17.4 and 11.0 Hz), 6.68 (1H, t, J 2.5 Hz), 7.40 (1H, s); MS (+ve ion electrospray) m/z 513 (MH$^+$, 100%).

EXAMPLE 21
{(1-Aza-bicyclo[2.2.2]oct-3-yl)-acetyl}-carbamic acid mutilin 14-ester Ethyl (1-aza-bicyclo[2.2.2]oct-3-yl)-acetate (European Patent 363085, October 1988) was hydrolysed by reflux for 5 hours in 8M hydrochloric acid. The resulting (1-aza-bicyclo[2.2.2]oct-3-yl)-acetic acid hydrochloride was used to prepare the title compound as a solid (9% overall): δ(CDCl$_3$) inter alia 3.32 (1H, d), 5.0–5.4 (2H, m), 5.61 (1H, d), 6.40 (1H, dd).

REFERENCE EXAMPLES

Example 87 of PCT/EP96/05874
Mutilin 14-[N-(1-ethyl-piperidin-4-oyl)]-carbamate
Step 1. Ethyl 1-ethyl-isonipecotate Ethyl isonipecotate (6.28 g) in ethanol (35 ml) was treated with ethyl iodide (6.86 g) and powdered potassium carbonate (10 g). The mixture was stirred and heated under reflux for 20 hours. The mixture was cooled to room temperature and the solid was removed by filtration and was washed with ethanol (2×10 ml). The ethanol was removed from the filtrate by evaporation under reduced pressure, and the resulting residue was partitioned between chloroform (100 ml) and water (50 ml). The organic layer was separated, washed with saturated sodium chloride solution, and dried (sodium sulphate). The solvent was removed by evaporation under reduced pressure to give the title compound as a yellow oil (6.62 g); MS(EI) m/z 185 (M+).
Step 2. 1-Ethyl-isonipecotic acid hydrochloride Ethyl 1-ethyl-isonipecotate (5.5 g) was dissolved in water (22 ml)/c.HCl (39 ml) and the solution was heated under reflux for 4 hours. The solvent was removed by evaporation under reduced pressure. The residue was dissolved in water (30 ml), and the water was removed by evaporation under reduced-pressure. The residue was triturated with toluene (50 ml), and the toluene was removed by evaporation under reduced pressure to give a solid which was dried in vacuo for 18 hours. The title compound was thus obtained as a white powder (5.4 g); MS(EI) m/z 157 (M+).

Step 3. (3R)-3-Deoxo-11-deoxy-3-methoxy-11-oxo-4-epi-mutilin 14-[N-(1-ethyl-piperidin-4-oyl)]-carbamate 1-Ethyl-isonipecotic acid hydrochloride (0.95 g) was suspended in thionyl chloride (8 ml) and the mixture was stirred and heated under reflux for 3 hours to give a clear yellow solution. The thionyl chloride was removed by evaporation under reduced pressure and the resulting residue was suspended in toluene (5 ml) and the toluene was removed by evaporation under reduced pressure to give 1-ethyl-isonipecotyl chloride hydrochloride as a white solid.

The acid chloride was suspended in dry dichloromethane (20 ml) and silver cyanate (1.5 g) was added. The mixture was stirred and heated under reflux for 1 hour. The mixture was cooled to room temperature and (3R)-3-deoxo-1-deoxy-3-methoxy-11-oxo-4-epi-mutilin (1 g) and triethylamine (0.5 g) were added. The mixture was stirred at room temperature for 16 hours. The mixture was diluted with ethyl acetate (50 ml) and the solid was removed by filtration. The filtrate was washed with saturated sodium bicarbonate and saturated sodium chloride. The solution was dried (sodium sulphate), and the solvent was removed by evaporation under reduced pressure to give a yellow gum. The gum was chromatographed on silica gel using 1:3 ethyl acetate/chloroform and 1:9:90 ammonia solution (35%)/methanol/dichloromethane to give the title compound as a colourless gum (134 mg); 1H NMR (CDCl3) inter alia 2.88 (2H, q. J 6.5 Hz), 3.08 (3H, m), 3.22 (3H, s), 3.42 (1H, m), 5.04 (1H, d, J 17.5 Hz), 5.33 (1H, d, J 10.7 Hz), 5.74 (1H, d, J 9.9 Hz), 6.63 (1H, dd, J 17.5, 10.7 Hz), 7.47 (1H, s).

Step 4. Mutilin 14-[N-(1-ethyl-piperidin-4-oyl)]-carbamate (3 R)-3-Deoxo-11-deoxy-3-methoxy-11-oxo-4-epi-mutilin 14-[N-(1-ethyl-piperidin-4-oyl)]-carbamate (110 mg) in 1,4-dioxane (0.7 ml) was treated with c.HCl (0.7 ml) and the solution was kept at room temperature for 2.5 hours. The solution was diluted with water (10 ml) and washed with dichloromethane (10 ml). The aqueous phase was basified by careful addition of solid potassium carbonate and the resulting mixture (pH 10) was extracted with chloroform (3×10 ml). The organic extract was dried (sodium sulphate) and the solvent was removed by evaporation under reduced pressure to give the title compound as a white solid (80 mg); 1 H NMR (CDCl3) inter alia 1.12 (3H, t, J 7.1 Hz), 2.48 (2H, q, J 7.1 Hz), 2.97 (3H, m), 3.37 (1H, dd, J 10.3, 6.6 Hz), 5.24 (1H, d, J 17.5 Hz), 5.37 (1H, d, J 11 Hz), 5.70 (1H, d, J 8.4 Hz), 6.50 (1H, dd, J 17.5, 11 Hz), 7.35 (1H, s); MS(EI) m/z 502 (M+).

Example 161 of PCT/EP96/05874
Mutilin 14-[N-(N-methylnipecotyl)carbamate]
Step 1. (3R)-3-Deoxo-11-deoxy-3-methoxy-11-oxo-4-epi-mutilin 14-[N-(N-methylnipecotyl)carbamate]

(±)-Ethyl N-methylnipecotate (5.0 g) was dissolved in 5M hydrochloric acid (100 ml) and stirred at room temperature for 16 h. The solution was then evaporated at reduced pressure and the residue re-evaporated from toluene (×2). Trituration gave the hydrochloride salt of (±)-N-methylnipecotic acid as a white solid (3.91 g).

The hydrochloride salt of (±)-N-methylnipecotic acid (1.0 g) was suspended in dichloromethane (25 ml) and stirred at room temperature for 2 h with oxalyl chloride (0.58 ml) and DMF (1 drop). The solvent was then evaporated to yield the hydrochloride salt of N-methylnipecotyl chloride as a pale yellow solid.

The above acid chloride (0.596 g) was suspended in dry dichloromethane and stirred at room temperature for 4 h with (3R)—deoxo-11-deoxy-3-methoxy- 11-oxo-4-epi-mutilin (0.334 g), silver cyanate (0.450 g) and triethylamine (0.276 ml). The suspension was then filtered through Celite, diluted with ethyl acetate and washed with water and saturated sodium chloride solution. The organic solution was dried (MgSO4), filtered and evaporated to yield the crude product. Silica gel column chromatography, eluting with a gradient of 0–5% 9:1 methanol/35% ammonia solution in dichloromethane gave the title compound as a diastereomeric mixture and as a colourless oil (0.290 g); 1H NMR (CDCl3) 0.85 and 0.88 (2×d, all 3H, J 6.9 Hz), 1.00 (3H, d, J 6.4 Hz), 1.05–1.85 (m), 1.20 (3H, s), 1.25 (3H, s), 1.9–2.40 (6H, m), 2.32 (3H, 2×s), 2.48 (1H, m), 2.69(1H, broad res.), 2.80–2.98 (3H, broad q,), 3.22 (3H, s), 3.40–3.53 (1H, m), 4.98 (1H, d, J 17.6 Hz), 5.29 (1H, d, J 10.7 Hz), 5.62–5.72 (1H, 2×d, J 9.9 Hz) and 6.78–6.91 (1H, m); MS (EI) m/z 503.

Step 2. Mutilin 14-[N-(N-methylnipecotyl)carbamate]

The product from step 1, (0.250 g) in 1,4-dioxan (3.0 ml) was stirred at room temperature for 4 h with conc. hydrochloric acid (2.0 ml). The solution was then diluted with ethyl acetate and neutralized with saturated sodium hydrogen carbonate solution. The organic solution was washed with saturated sodium chloride solution, dried (MgSO4) and evaporated to yield the crude product. After purification by silica gel chromatography, eluting with a gradient of 0–5% 9:1 methanol/35% ammonia solution in dichloromethane, the title compound was isolated as a diastereoisomeric mixture and as a white foam, (0.205 g); 1H NMR (CDCl3) 0.78 (3H, 2×d, J 6.7 Hz), 0.89 (3H, d, J 7.0 Hz), 1.19 (3H, s), 1.35–2.40 (m), 1.47 (3H, s), 2.30 (3H, 2×s),2.63–2.90 (2H, broad res.), 3.35 (1H, broad res.), 5.22 (1H, d, J 17.4 Hz), 5.39 (1H, dd. J 1.4,11.0 Hz), 5.60–5.72 (1H, 2×d, J 8.5 Hz), and 6.63 (1H, dd, J 11.0,17.4 Hz); MS (EI) m/z 488.

What is claimed is:

1. A compound of formula (3), or a pharmaceutically acceptable salt thereof:

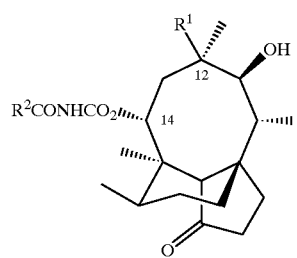

(3)

in which:
R$^1$ is vinyl or ethyl; and
R$^2$ is a group R$^3$, R$^4$CH$_2$—, or R$^5$R$^6$C═CH—; wherein each of R$^3$ and R$^4$ is an azabicyclic ring system or R$^5$ and R$^6$ together with the carbon atom to which they are attached form an azabicyclic ring system.

2. A compound according to claim 1, wherein each azabicyclic ring system is selected from the group consisting of azabicyclo[2.2.2]octyl, azabicyclo[2.2.1]heptyl, azabicyclo[3.2.1]octyl, azabicyclo[4.4.0]decyl, quinuclidinyl, azabicyclo[3.2.1]octenyl, and azabicyclo[3.3.1]non-5-yl.

3. A compound selected of formula (3) as defined in claim 1 selected from:
(1-Aza-bicyclo[2.2.2]octane-4-carbonyl)-carbamic acid mutilin 14-ester;
(1-Aza-bicyclo[2.2.2]octane-4-carbonyl)-carbamic acid mutilin 14-ester hydrochloride;

3 (1-Aza-bicyclo[2.2.1]heptane-4-carbonyl)-carbamic acid mutilin 14-ester;

{(3S,4R)-1-Aza-bicyclo[2.2.1]heptane-3-carbonyl}-carbamic acid mutilin 14-ester;

{(3S,4R)-1-Aza-bicyclo[2.2.1]heptane-4-carbonyl}-carbamic acid 14-deoxy-19,20-dihydro-mutilin 14-ester;

(1-Aza-bicyclo[2.2.2]octane-4-carbonyl)-carbamic acid 14-deoxy-19,20-dihydro-mutilin 14-ester;

(1-Aza-bicyclo[2.2.2]octane-3-carbonyl)-carbamic acid mutilin 14-ester;

{(3S ,4R)-1-Aza-bicyclo[2.2.1]heptane-3-carbonyl}-carbamic acid mutilin 14-ester hydrochloride;

(1-Aza-bicyclo[3.2.1]octane-5-carbonyl)-carbamic acid mutilin 14-ester;

(1-Aza-bicyclo[2.2.2]octane-2-carbonyl)-carbamic acid mutilin 14-ester;

{(3R,4S)-1-Aza-bicyclo[2.2.1]heptane-3-carbonyl}-carbamic acid mutilin 14-ester;

{(3R,4S)-1-Aza-bicyclo[2.2.1]heptane-3-carbonyl}-carbamic acid mutilin 14-ester hydrochloride;

{(3R,4R)-1-Aza-bicyclo[2.2.1 ]heptane-3-carbonyl}-carbamic acid mutilin 14-ester hydrochloride;

{(3S,4S)-1-Aza-bicyclo[2.2.1]heptane-3-carbonyl}-carbamic acid mutilin 14-ester hydrochloride;

(1-Aza-bicyclo[4.4.0]decane-4-carbonyl)-carbamic acid mutilin 14-ester hydrochloride (equatorial isomers);

(1-Aza-bicyclo[4.4.0]decane-4-carbonyl)-carbamic acid mutilin 14-ester hydrochloride (axial isomers);

{(1-Aza-bicyclo[4.4.0]dec-4-yl)-acetyl}-carbamic acid mutilin 14-ester;

(1-Aza-bicyclo[3.2.1 ]oct-3-ene-3-carbonyl)-carbamic acid mutilin 14-ester;

(1-Aza-bicyclo[3.3.1]nonane-5-carbonyl)-carbamic acid mutilin 14-ester;

{(1-Aza-bicyclo[2.2.2]oct-3-ylidene)-acetyl}-carbamic acid mutilin 14-ester; and {(1-Aza-bicyclo[2.2.2]oct-3-yl)-acetyl}-carbamic acid mutilin 14-ester.

4. A pharmaceutical composition comprising a compound according to claim 1 together with a pharmaceutically acceptable carrier or excipient.

5. A method of treating microbial infections in animals, which method comprises the step of administering an antimicrobially effective amount of a compound according to claim 1 to a patient in need thereof.

6. A method for preparing a compound of formula (3) according to claim 1, which comprises reacting a compound of formula (4) where X is hydrogen or a hydroxyl protecting group, or a compound of formula (5), with an acyl isocyanate of formula $R^3CONCO$, $R^4CH_2CONCO$, or $R^5R^6C{=}CHCONCO$

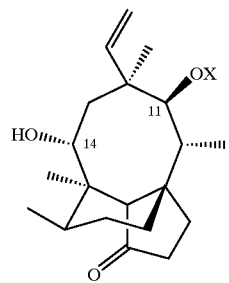

(4)

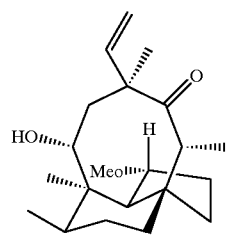

(5)

7. A process according to claim 6, which comprises reacting a compound of formula (4) with a compound of formula $R^3COCl$, $R^4CH_2COCl$, or $R^5R^6C{=}CHCOCl$ in the presence of silver cyanate and a base, wherein each of $R^3$ to $R^6$ is protected where appropriate, and thereafter carrying out one or more of the following steps in any desired order:

deprotecting a group X to generate a hydroxyl group at position 11, deprotecting a protected group $R^3$ to $R^6$, and hydrogenating the vinyl group at position 12 to form an ethyl group.

8. A process according to claim 6, which comprises reacting a compound of formula (5) with a compound of formula $R^3COCl$, $R^4CH_2COCl$, or $R^5R^6C{=}CHCOCl$ in the presence of silver cyanate and a base, wherein each of $R^3$ to $R^6$ is protected where appropriate, and thereafter carrying out one or more of the following steps in any desired order:

treating the product with acid to give a compound of formula (3), deprotecting a protected group $R^3$ to $R^6$, and hydrogenating the vinyl group at position 12 to form an ethyl group.

* * * * *